United States Patent [19]

Chmelir et al.

[11] Patent Number: 4,605,401

[45] Date of Patent: Aug. 12, 1986

[54] MATERIAL FOR THE ABSORPTION OF WATER, AQUEOUS SOLUTIONS AND AQUEOUS BODY FLUIDS

[75] Inventors: Miroslav Chmelir; Alois Künschner, both of Krefeld, Fed. Rep. of Germany

[73] Assignee: Chemische Fabrik Stockhausen GmbH, Krefeld, Fed. Rep. of Germany

[21] Appl. No.: 614,353

[22] Filed: May 25, 1984

Related U.S. Application Data

[63] Continuation of Ser. No. 434,218, Oct. 14, 1982, abandoned.

[30] Foreign Application Priority Data

Oct. 16, 1981 [DE] Fed. Rep. of Germany ....... 3141098

[51] Int. Cl.⁴ ............................................. A61F 13/16
[52] U.S. Cl. .................... 604/368; 427/396; 428/290; 428/264; 428/274; 428/511; 428/284; 428/286; 428/507
[58] Field of Search ............... 428/284, 286, 290, 264, 428/274, 507, 511, 514; 604/368, 275, 376, 378; 427/396

[56] References Cited

U.S. PATENT DOCUMENTS

| | | | |
|---|---|---|---|
| 2,905,568 | 9/1959 | Burgeni | 427/244 X |
| 3,670,731 | 6/1972 | Harmon | 604/368 |
| 3,922,434 | 11/1975 | Lindgren et al. | 428/342 |
| 4,062,451 | 12/1977 | Gander | 428/286 X |
| 4,071,650 | 1/1978 | Gross | 428/290 X |
| 4,293,609 | 10/1981 | Erickson | 428/284 X |
| 4,310,593 | 1/1982 | Gross | 428/290 |
| 4,338,371 | 7/1982 | Dawn et al. | 428/284 X |
| 4,413,995 | 11/1983 | Korpman | 428/286 X |
| 4,424,247 | 1/1984 | Erickson | 428/284 X |

FOREIGN PATENT DOCUMENTS

3036415 4/1981 Fed. Rep. of Germany .
3037507 4/1981 Fed. Rep. of Germany .

*Primary Examiner*—George F. Lesmes
*Assistant Examiner*—N. B. Swisher
*Attorney, Agent, or Firm*—Sprung, Horn, Kramer & Woods

[57] ABSTRACT

An absorption material is produced by applying directly to a support in the presence of liquid an absorbent which is at least partially water-softened, and drying to remove the liquid so as to leave the absorbent directly on the support. The support may be fibrous or particulate like sawdust or it may be a textile sheet or paper. The absorbent may be an acrylic based polymer. Because the absorbent directly contacts the support the product has increased absorptive capacity and is stronger, making it especially useful as a diaper, tampon, sanitary napkin, surgical dressing, battery separator and/or filter for cigarette smoke or for liquids.

12 Claims, No Drawings

MATERIAL FOR THE ABSORPTION OF WATER, AQUEOUS SOLUTIONS AND AQUEOUS BODY FLUIDS

This is a continuation of application Ser. No. 434,228, filed Oct. 14, 1982, now abandoned.

BACKGROUND OF THE INVENTION

The invention relates to an absorption material, a method for the manufacture thereof, and its use as an absorbent for water, water vapor, aqueous solutions, aqueous or serous body fluids such as urine or blood, and for the absorption, retention and subsequent controlled release of water, aqueous solutions and/or the components dissolved therein, to other bodies.

In recent years a number of different polymers have been developed which have a high capacity for the absorption of water and body fluids. The majority of the products are manufactured on a starch basis, such as for example starch acrylonitrile graft polymers (U.S. Pat. Nos. 3,997,484, 3,661,815, 4,155,888 and 3,935,099), gelatinized starch derivatives (DE OS No. 2,702,781), starch acrylamide acrylamidopropanesulfonic acid graft polymer (U.S. patent application Ser. No. 955,827, filed 10-30-1978) or on a cellulose basis, such as derivatives of alkyl or hydroxyalkyl cellulose (JA Pat. No. 11/125,481), carboxymethylcellulose (BE Pat. No. 862,130, GB Pat. No. 1,159,949), and on a polysaccharide basis (DE OS No. 2,650,377). The all-synthetic absorbents described in numerous patents include crosslinked polymers and copolymers on an acrylic or methacrylic acid basis (DE OS No. 2,429,236, DE OS No. 2,614,662, U.S. Pat. Nos. 4,018,951, 3,926,891, 4,066,583 and 4,062,817, DE OS No. 2,712,043, DE OS No. 2,653,135, DE OS No. 2,813,635), or maleic acid derivatives (U.S. Pat. No. 4,041,228).

All these products are virtually insoluble in water and absorb a multiple of their weight in water, urine or other aqueous solutions.

Since these products are in a powder-like form, their incorporation into the end products (e.g., diapers, bandages etc.) is difficult and requires complex and expensive proportioning apparatus and applicators. It is especially difficult to handle a finely ground product of a grain size under 100 micrometers. The powder product adheres but poorly to the support, so that as a rule an adhesive must be used, and part of the absorption capacity of the powdered product is lost on that account.

Processes are also known for the preparation of absorbent fiber mixtures, in which a polymeric hydrophilic component, such as polyacrylic acid, carboxymethylcellulose etc., is admixed with the spinning solution, so that fibers of increased absorbency develop, as can be seen in German OS Nos. 2,550,345, 2,750,622, 2,750,900, 2,751,833, 2,905,424 and 3,036,415, and German Pat. No. 2,634,995. The hydrophilic component must be completely soluble in water and in the spinning solution. Since the weight ratio of the hydrophilic polymer component to the fiber component in these fiber mixtures is always less than 1, this also greatly limits the absorbency. In accordance with published European patent application No. 0023561, an improved absorbency is achieved in cellulose fibers by converting them in an inert medium to partially crosslinked, anoxidized carboxyalkylcellulose. Published European Application No. 0009322 describes the preparation of an absorbent paper from mixtures of cellulose fibers with insoluble fibers of amine-formaldehyde resin, in which a certain "freeness" (=degree of grinding) condition must be maintained.

On account of the great ability of polymeric absorbents to absorb water, it is quite difficult to incorporate these substances into the finished product out of an aqueous suspension, as in the case of paper manufacture. Either fiber suspensions of very low solid content (less than 0.1%, cf. DE OS No. 3,037,507) must be used in preparing the absorbent material, or the incorporation of the absorbent into the finished product can be accomplished (but only in the case of a carboxyl-containing absorbent) in two phases: first the absorbent is suspended in water in its acid form together with the fiber components, the paper web is formed on a paper machine and dried; the paper web is then neutralized in another step in order to achieve the desired absorbency of the finished product. The maximum ratio of the polymer component to the fiber component in the suspension is given as 65:35 by weight (DE OS No. 3,040,965).

Therefore an absorbent material would be desirable which would be very simple to make but would have a very high absorption capacity. Particularly desirable would be an absorption material in which the absorbent is anchored or fixed very firmly on or in the support, without any additional adhesives. Quite particularly advantageous would be an absorption material in flat form, such as a woven or nonwoven fabric, the absorbent being fixed in or on the flat support material. Such an absorption material ought to contain a very large amount of absorbent.

Setting out from known absorption materials consisting of a polymeric absorbent and a support, it is therefore the object of the invention to improve such an absorption material and avoid its disadvantages, especially to create an absorption material in which the absorbent is fixed permanently in or on the support without additional adhesives.

SUMMARY OF THE INVENTION

This object is achieved by an absorption material consisting of an absorbent permanently fixed on or in a support material, the absorption material of the invention having been obtained by treating the support material with the at least partially water-softened absorbent and drying.

Preferred is an absorption material of the invention whose absorbent has been softened with an organic solvent containing water.

Both flat materials and discrete particles are suitable as support material, although for the purposes of the invention flat supports, such as sheets, webs or plates are preferred. Suitable materials are, for example, webs of textile fabric, nonwovens, paper sheets or webs, but also glass, ceramic and metal plates. For the purposes of the invention, special preference is given to webs or sheets of textile fabric or paper, as well as nonwovens. Of the materials other than flat materials, artificial or natural fibers, such as cellulose or synthetic fibers, which can be made into flat materials, are especially suitable. In addition, however, other particulate support materials are suitable, such as wood flour (sawdust) and sand, for example.

Suitable absorbents, which are preferably in powder form, are both the moisture-absorbent polymers on the basis of polysaccharides, such as cellulose, cellulose derivatives such as carboxymethylcellulose, alkyl- or hydroxyalkylcellulose, starch and starch derivatives, and vegetable gums (e.g., xanthan gum), alginic acid and its salts, and also the polymers or copolymers on a basis of (meth)acrylic acid or (meth)acrylic acid derivatives, these being primarily the homopolymers or copolymers of acrylic, methacrylic, acrylamidomethylpropanesulfonic acid, or of the salts of these acids, or of acrylamide or methacrylamide with one another or with vinylpyrrolidone and/or vinyl acetate. The above polymers can be crosslinked by an at least bifunctional crosslinking agent, so that they can only be softened by water, but will not be soluble. All of these polymers are made by known methods.

The absorption material of the invention consists of fiber material and absorbent in a weight ratio of 10 to 99.9%, preferably 20 to 75%, of fiber by weight, and 0.1 to 90, preferably 25 to 80%, of the absorbent. The absorption material of the invention can accordingly consist almost entirely of absorbent and yet will have the advantage of a flat material.

The absorption material of the invention can additionally contain perfumes, binding agents or other secondary substances, such as disinfectants for example, provided they do not adversely affect the absorptive properties of the absorption material.

The absorption material of the invention is prepared by treating the support material with the at least partially water-softened absorbent and then drying. Preferably the absorption material is made with at least one organic solvent containing water and with at least one partially moistened absorbent, and then dried.

A variety of solvents miscible with water can be used as organic solvents, preferably methanol, ethanol, isopropanol, acetone, tetrahydrofuran, dioxane, glycerin, or ethylene glycol, all containing 0.1 to 60% of water.

In accordance with the preferred method of preparation, the at least partially water-softened absorbent is worked into a particulate support which is preferably a fibrous material such as cellulose or a textile fiber, and the mixture is flattened out and dried. In this manner an absorption material in flat form is immediately obtained. In this method of procedure it is best to mix the absorbent with the fiber in the presence of an organic solvent containing water. The fibrous support is suspended in an organic solvent which can contain up to 60% water (for practical purposes a water content of 10 to 20% suffices), and is mixed with the powdered absorbent, which for the sake of better miscibility is preferably also suspended in the organic solvent containing, if desired, water. From this suspension a fiber web is produced, for example by applying the suspension to a sieve or suction sieve, removing the excess solvent with the aid of a vacuum, and drying the resultant sheet. The drying can be performed at normal temperature, preferably at elevated temperatures.

Surprisingly, the partially water-softened particles of the absorbent simultaneously serve as binding agents and dry strengtheners for the fiber of the support material. An absorbent flat material can therefore be produced, having a variable amount, or in case of necessity an extremely great amount, of absorbent without the use of an additional binding agent and dry strengthener for the flat material, such as otherwise commonly used in paper manufacture. Thus, depending on the moisture content of the absorption material particles, which can also be controlled by the solvent and/or moisture content, paper sheets or nonwovens of different dry strengths can be obtained, in which the absorbent is an integral component of the material and thus is fixed firmly and permanently, without additional adjuvants.

Other particulate supports, such as sawdust, can be made in this manner into an absorption material in flat form. Such products can be used, for example, for soil improvement or strengthening.

Surprisingly, by treating a support like cotton batting, for example, which has only a low tensile strength, it is possible to achieve a very great improvement of the strength characteristics.

It is furthermore surprising that especially good results are achieved with absorbents in powder form of a grain size smaller than 200, especially smaller than 100 micrometers.

Such grain sizes are very hard to incorporate in the powder state.

In an additional method of manufacture, the absorption material of the invention is obtained by applying the at least partially water-softened absorbent to the surface of a support, preferably a support in flat form. The support can be dry or slightly moistened. The water-softened absorbent can be applied by spraying or brushing, followed by drying. The absorbent is advantageously applied in the form of a suspension in the aqueous-organic solvent.

In both variants, the fixing of the absorbent in or on the support material is accomplished by drying and/or the application of pressure, no additional binding agents being required, as a rule, for the fixing of the absorbent on the support.

The absorption material of the invention, on account of its composition, is suitable for the absorption and/or retention of water, water vapor, aqueous solutions and body fluids, such as urine or blood, especially for use in absorbent disposable products such as baby diapers, sanitary napkins or tampons or in absorbent products for surgical and medical use.

Furthermore, the absorption material of the invention, when saturated with water or aqueous solutions, can be used for the controlled release of water or of components dissolved in water to other bodies, such as plants for example, or they can be used as nutrient medium for various cultures, in the controlled release of medication, and also for technical purposes in conjunction with storage battery fluids, filtration, etc.

The invention is illustrated by the following examples.

EXAMPLES

Example 1

Three grams of cellulose were suspended in 300 milliliters of 96% ethanol in a vessel and whipped with a highspeed beater. Then 3 g of absorbent (crosslinked polyacrylic acid) was suspended in 50 ml of ethanol and mixed with the whipped cellulose fiber suspension. The mixture was then placed on a suction filter (diam. 20 cm), the solvent was removed, and the sheet that had formed was dried at 85° C.

The sheet had the following composition:
cellulose fibers: 95 g/m$^2$
absorbent: 95 g/m$^2$
total specific weight: 190 g/m$^2$.

The absorption of the product was tested on a sheet of 16 square centimeters, with water and model urine solution (2.0% urea, 0.9% NaCl, 0.1% MgSO$_4$ and 0.06% CaCl$_2$ dissolved in distilled water).

The absorption capacity of this sheet was as follows:
31.1 ml: model urine solution per gram 198. ml: water per gram.

Example 2

As in Example 1, 3 g of cellulose was suspended in 300 ml of 96% ethanol and whipped with a high-speed beater. Then 9 g of absorbent (crosslinked polyacrylic acid) was suspended in 50 ml of 96% ethanol and mixed with the whipped cellulose fibers. The mixture was then placed on a suction filter (diam. 20 cm), the solvent was removed, and the cellulose sheet was dried at 85° C.

The sheet had the following composition:
cellulose fibers: 95 g/m$^2$
absorbent: 285 g/m$^2$
total specific weight: 380 g/m$^2$ The absorption capacity of this sheet, tested as in Example 1, was as follows:
35.5 ml of model urine solution per gram
202 ml of water per gram

Example 3

As in Example 2, 3 g of cellulose was whipped in a variety of organic solvents and in organic solvents containing water mixed with 9 g of polymeric absorbent (crosslinked polyacrylic acid), prepared in the same manner, and tested as in Example 2. The mechanical dry strength of the sheet was determined with a bursting strength tester, the sheet being affixed by pressing onto a paper support having a bursting strength of 15.0 N/cm$^2$.

| Solvent | Absorption capacity model urine solution | (ml/g) water | Bursting strength N/cm$^2$ |
|---|---|---|---|
| Toluene | 23.8 | 150 | 15.0* |
| Tetrahydrofuran | 26.3 | 171 | 15.5* |
| Tetrahydrofuran/water 90:10 | 35.6 | 188 | 18.0 |
| Dioxane/water 98:2 | 35.9 | 175 | 16.0 |
| Acetone | 29.2 | 151 | 15.1* |
| Acetone/water 90:10 | 40.9 | 152 | 18.8 |
| Methanol/water 98:2 | 32.7 | 185 | 22.5 |
| Methanol/water 95:5 | 32.5 | 198 | 23.5 |
| Methanol/water 90:10 | 26.7 | 195 | 25.3 |
| Methanol/water 80:20 | 36.3 | 190 | 24.0 |
| Ethanol/water 95:5 | 37.5 | 210 | 23.7 |
| Ethanol/water 90:10 | 38.3 | 201 | 25.3 |

*No bond was produced between the fiber and the absorbent.

Example 4

As in Example 2, 3 g of ground cellulose was mixed with various amounts of polymeric absorbent (crosslinked sodium salt of polyacrylic acid) in a 90:10 mixture of methanol and water, treated in the same manner, and tested as in Example 3:

| Composition | | | Absorption capacity (ml/g) | |
|---|---|---|---|---|
| Cellulose fiber g/m$^2$ | Absorbent g/m$^2$ | Specific wt. g/m$^2$ | model urine solution | Water |
| 95 | 32 | 127 | 31.4 | — |
| 95 | 95 | 190 | 35.7 | 195 |
| 95 | 380 | 475 | 40.8 | — |
| 95 | 570 | 665 | 37.2 | — |
| 95 | 860 | 955 | 38.4 | 120 |

Example 5

In accordance with Example 2, 3 g of ground cellulose was mixed with various absorbents (9.0 g in each case) in a 90:10 mixture of methanol and water, and treated in the same manner as in Example 3.

| Absorbent | Absorption capacity (ml/g) | | Bursting strength N/cm$^2$ |
|---|---|---|---|
| | Model urine | water | |
| Polyacrylamide mol. wt. 5 × 10$^6$ g/ml | 5.1 | 4.8 | 20.3 |
| Acrylamide/acrylic acid copolymer 65:35, mol. wt. 6 × 10$^6$ g/ml | 5.5 | — | 23.5 |
| Carboxymethylcellulose | 7.7 | 8.8 | — |
| Calcium alginate/sodium salt | 10.5 | 10.5 | — |
| Methylhydroxyethyl-cellulose | 5.4 | 5.1 | 25.0 |
| Crosslinked starch-acrylic acid copolymer | 15.5 | 45.1 | — |

Example 6

In accordance with Example 2, 3 g of rayon staple fiber of 1.7/6 dtex/mm was mixed with 8 g of polymeric abosrbent (crosslinked polyacrylic acid) in a 90:10 mixture of methanol and water and treated in the same manner as in Example 2. In addition to the absorption capacity for water and model urine, the absorption capacity for human blood under compressive stress (32 g/cm$^2$) was tested.

The absorption capacity of this material was
152 ml of water per gram
36.6 ml of model urine solution per gram
3.9 ml of blood per gram

Example 7

In accordance with Example 2, 1.5 g of rayon staple fibers of 1.7/6 dtex/mm was mixed with 1.5 g of cellulose and 9 g of polymeric absorbent (crosslinked polyacrylic acid) in a 90:10 mixture of methanol and water, and treated in the same manner as in Example 2. In addition to the capacity for the absorption of water and model urine, a test was also made of the ability to absorb human blood under compressive stress (32 g/cm$^2$). The absorption capacity of this material was:
120 ml of water per gram
22.5 ml of model urine per gram
3.8 ml of blood per gram

Example 8

A crosslinked polyacrylic acid sodium salt in the form of a suspension in a 90:10 mixture of methanol and water was sprayed onto a nonwoven fabric prepared from rayon staple fibers of 1.7/34 dtex/mm, and fixed on the fabric by drying at 85° C. The coated fabric had the following composition:
Cellulose fibers: 78 g/m$^2$
Absorbent: 23 g/m$^2$ The absorption capacity of this material amounted to
65 ml of water per gram
21.6 ml of model urine solution per gram
3.5 ml of blood per gram

Example 9

Crosslinked polyacrylic acid sodium salt was sprayed in the form of a suspension in a 90:10 mixture of methanol and water onto a nonwoven fabric prepared from polypropylene staple fibers of 1.7/45 dtex/mm, and fixed on the fabric by drying at 85° C. The coated fabric had the following composition:

Polypropylene fibers: 70 g/m²
Absorbent: 21 g/m²
The absorption capacity of this material was
58 ml of water per gram
20.5 ml of model urine solution per gram Example 10

A paste prepared from 50 g of crosslinked acrylic acid/acrylamidomethylpropanic acid copolymer in a ratio of 90:10 in 100 g of a 50:40:10 mixture of methanol, glycerine and water was spread in a thin layer onto a nonwoven fabric prepared from polyester staple fibers of 1.7/34 dtex/mm, and the absorbent was fixed on the fabric by drying at 95° C. The coated fabric contained 55 g of absorbent per square meter and its absorption capacity was
112 ml of water per gram or
36 ml of model urine solution per gram.

Example 11

A crosslinked acrylic acid sodium salt acrylamide copolymer in a ratio of 90:10 was applied in the form of a suspension in a 95:5 mixture of ethanol and water on the filterpaper ($\phi$18 cm, 85 g/m²) and dried at 90° C. The material contained 60 g of the square meter and its absorption capacity was
19.2 ml of model urine solution per gram
55 ml of water per gram.

Example 12

0.75 g of a crosslinked polyacrylic acid sodium salt in the form of a suspension in a 90:10 mixture of ethanol and water was sprayed onto glass plates of an area of 100 square centimeters and affixed to the plates by drying at standard temperature. The dried coating of absorbent binds 217 g of water or 29.5 ml of model urine solution.

Example 13

10 g of wood flour was treated at standard temperature for 10 minutes with a suspension of 10 g of absorbent crosslinked polyacrylic acid) in 20 g of a mixture of methanol and water, and then dried at 80° C. The absorption capacity of this material amounted to
65 ml of water per gram
18.5 ml of model urine solution per gram
3.1 ml of blood per gram Example 14

A sheet of paper (80 g/m²) was moistened with 80 g/m² of a 60:40 mixture of water and methanol and sprinkled with finely pulverized crosslinked polyacrylic acid sodium salt (grain size less than 100 micrometers) and then dried at 100° C. The material contained 60 g of the absorbent per square meter. The absorption capacity of this sheet was
10.5 ml of model urine solution per gram
12.5 ml of water per gram Example 15

200 g of peat were treated in a vessel with a suspension of 200 g of crosslinked polyacrylic acid in 3600 g of a 90:10 mixture of ethanol and water at standard temperature for 15 minutes and then dried at 90° C. The result was a material with an absorbent bound to it in an attrition-resistant manner, having the following absorption capacities:
122 ml of water per gram
44 ml of 0.1% NaCl solution
24 ml of 1.0% NaCl solution
27 ml of model urine solution.

Example 16

Preparation of a Crosslinked Synthetic Polymer 328 g of acrylic acid and 2.6 g of N,N'-methylenebisacrylamide were dissolved in 980 g of water in a polymerization vessel, and adjusted to pH 4.0 with 127.5 g of sodium hydrogen carbonate. At standard temperature the components of the catalyst system (0.36 g of azobisamidinepropanedihydrochloride, 0.73 g of potassium persulfate, 1.34 g of sodium pyrosulfite and 0.06 g of iron(II) gluconate), dissolved in 120 ml of water, were added, whereupon adiabatic polymerization took place. The resultant polymer gel was crushed, dried and ground.

Example 17

Preparation of a Crosslinked Synthetic Copolymer 320 g of acrylic acid, 56 g of vinylpyrrolidone and 3.75 g of N,N'-methylenebisacrylamide were dissolved in a polymerization vessel in 862 g of water and neutralized with 100 g of sodium hydrogen carbonate to pH 4.4. At standard temperature the individual components of the catalyst system (0.6 g of azobisamidine-propanedihydrochloride, 1.2 g of sodium pyrosulfite and 0.6 g of potassium persulfate), dissolved in 150 g of water, were measured in. The polymerization takes place virtually adiabatically. The resultant polymer gel was crushed, dried and ground.

It will be understood that the specification and examples are illustrative but not limitative of the present invention and that other embodiments within the spirit and scope of the invention will suggest themselves to those skilled in the art.

We claim:

1. A process for producing an absorption material comprising applying directly to a cellulosic fibrous support a suspension in a liquid of a water-insoluble cross-linked absorbent polymer or copolymer of acrylic, methacryclic or acrylamidomethylpropanesulfonic acid or of a salt thereof, or of acrylic amide or methacrylic amide with one another or with at least one of vinylpyrrolidone and vinyl acetate, and drying to remove the liquid so as to leave the absorbent directly on the support.

2. The process according to claim 1, wherein the absorbent is applied as a water-containing suspension in an organic solvent.

3. The process according to claim 1, wherein the support is in the form of a web, sheet or plate.

4. An absorption material produced by the process of claim 3.

5. The process according to claim 1, wherein the support is a woven, knit or non-woven textile fabric or paper sheet.

6. An absorption material produced by the process of claim 5.

7. The process according to claim 1, wherein the support comprises fibrous material which is initially suspended.

8. The process according to claim 1, wherein the liquid comprises at least one member selected from the group consisting of methanol, ethanol, isopropanol, acetone, tetrahydrofuran, dioxane and glycerine having a water content of about 0.1 to 60% by volume.

9. An absorption material produced by the process of claim 1.

10. An absorption material according to claim 9, wherein the support comprises about 10 to 99.9 weight percent thereof and the absorbent about 90 to 0.1 weight percent thereof.

11. A diaper, tampon, sanitary napkin or surgical dressing comprising an absorption material according to claim 9.

12. The process according to claim 1, wherein the absorbent is a water-insoluble cross-linked polymer or copolymer of acrylic acid or of a salt thereof.

* * * * *

UNITED STATES PATENT AND TRADEMARK OFFICE
CERTIFICATE OF CORRECTION

PATENT NO. : 4,605,401

DATED : August 12, 1986

INVENTOR(S) : Miroslav Chmelir, et al.

It is certified that error appears in the above-identified patent and that said Letters Patent are hereby corrected as shown below:

Column 1, line 6            Delete "434,228" and substitute --434,218--

Signed and Sealed this

Tenth Day of February, 1987

Attest:

DONALD J. QUIGG

*Attesting Officer*      *Commissioner of Patents and Trademarks*